US012708769B2

(12) United States Patent
Pachon-Mateos et al.

(10) Patent No.: US 12,708,769 B2
(45) Date of Patent: Aug. 18, 2026

(54) EXTRACARDIAC AUTONOMIC NERVE STIMULATION

(71) Applicants: Jose Carlos Pachon-Mateos, São Paulo (BR); Enrique Indalécio Pachon-Mateos, São Paulo (BR); Carlos Thiene Cunha Pachon, São Paulo (BR)

(72) Inventors: Jose Carlos Pachon-Mateos, São Paulo (BR); Enrique Indalécio Pachon-Mateos, São Paulo (BR); Carlos Thiene Cunha Pachon, São Paulo (BR)

(73) Assignees: Jose Carlos Pachon-Mateos, São Paulo (BR); Enrique Indalécio Pachon-Mateos, São Paulo (BR); Carlos Thiene Cunha Pachon, São Paulo (BR)

( * ) Notice: Subject to any disclaimer, the term of this patent is extended or adjusted under 35 U.S.C. 154(b) by 59 days.

(21) Appl. No.: 15/948,298

(22) Filed: Apr. 9, 2018

(65) Prior Publication Data

US 2019/0091475 A1 Mar. 28, 2019

Related U.S. Application Data

(60) Provisional application No. 62/485,956, filed on Apr. 16, 2017.

(51) Int. Cl.

*A61N 1/36* (2006.01)
*A61N 1/05* (2006.01)
*A61N 1/362* (2006.01)

(52) U.S. Cl.

CPC ....... *A61N 1/36053* (2013.01); *A61N 1/0551* (2013.01); *A61N 1/056* (2013.01);

(Continued)

(58) Field of Classification Search

CPC ............ A61N 1/36014; A61N 1/36053; A61N 1/0456

See application file for complete search history.

(56) References Cited

U.S. PATENT DOCUMENTS 6,341,236 B1 * 1/2002 Osorio .............. A61N 1/36053 607/45
2006/0135998 A1 * 6/2006 Libbus .............. A61N 1/36117 607/2
2014/0046407 A1 * 2/2014 Ben-Ezra ........... A61N 1/36053 607/62

FOREIGN PATENT DOCUMENTS

WO WO-2013018083 A2 * 2/2013 ......... A61N 1/36017

OTHER PUBLICATIONS

Arruda, Mauricio et al., “Ablation of permanent AF: Adjunctive strategies to pulmonary veins isolation: Targeting AF NEST in sinus rhythm and CFAE in AF,” J Interv Card Electrophysiol (2008) 23:51-57.

(Continued)

*Primary Examiner* — Michael J D’Abreu
(74) *Attorney, Agent, or Firm* — Faegre Drinker Biddle & Reath LLP

(57) ABSTRACT

The ExtraCardiac Nerve Stimulator and the ExtraCardiac Nerve Stimulation (ECANS) are, respectively, the apparatus and method to get remote nerve stimulation for medical applications. The system makes possible the stimulation without direct contact with the nerve based on special electrical wave. The remote nerve stimulation is extremely important for investigational and therapeutic proposals. The possibility of having this resource without surgical dissection, nerve exposure and tissue lesion with time-consuming process, is remarkable. This procedure relies on a settable stimulator with special features that releases a pulse wave with high frequency, very short pulse width, great amplitude, (Continued)

and precise current and time limitation connected to a special catheter, placed inside a vase or viscera. Frequency, pulse width, amplitude and time of application are operator adjustable to be effective against large patient variations, different anatomy, and areas of application. Special features prevent the application of the stimulus in the heart.

11 Claims, 9 Drawing Sheets

(52) U.S. Cl.
CPC ...... *A61N 1/36057* (2013.01); *A61N 1/36114* (2013.01); *A61N 1/36139* (2013.01); *A61N 1/3615* (2013.01); *A61N 1/36167* (2013.01); *A61N 1/36171* (2013.01); *A61N 1/36175* (2013.01); *A61N 1/36178* (2013.01); *A61N 1/3621* (2013.01)

(56) References Cited

OTHER PUBLICATIONS

Calo, Leonardo et al., "Catheter Ablation of Right Atrial Ganglionated Plexi in Patients With Vagal Paroxysmal Atrial Fibrillation," Circ Arrhythm Electrophysiol. Feb. 2012; 5(1):22-31.
Chang, Hung-Yu et al., "Relationship Between Intrinsic Cardiac Autonomic Ganglionated Plexi and the Atrial Fibrillation Nest," Circ J. 2014; 78(4):922-8.
Chiou, Chuen-Wang et al., "Efferent Vagal Innervation of the Canine Atria and Sinus and Atrioventricular Nodes," Circulation, vol. 95, Issue 11, Jun. 3, 1997; pp. 2573-2584.
Das G., "Therapeutic review. Cardiac effects of atropine in man: an update," Int J Ciin Pharmacol Ther Toxicol. Oct. 1989; 27(10); only Abstract attached.
Lemola, Kristina et al., "Pulmonary Vein Region Ablation in Experimental Vagal Atrial Fibrillation: Role of Pulmonary Veins Versus Autonomic Ganglia," Circulation, Jan. 29, 2008; 117(4):470-7.
Lin, Venn-Jiang et al., Mapping of the Atrial Electrogram in Sinus Rhythm and Different Atrial Fibrillation Substrates. In: Shenasa M. Hindricks G. Borggrefe M, Breithardt, G—Cardiac Mapping. Wiley-Blackwell 4th Edition. 2013: pp. 599-600, 603, 649 and 651.
Hugh, Calkins et al., "2012 HRS/EHRA/ECAS Expert Consensus Statement on Catheter and Surgical Ablation of Atrial Fibrillation: Recommendations for Patient Selection, Procedural Techniques, Patient Management and Follow-up, Definitions, Endpoints, and Research Trial Design," Europace (2012) 14, 528-606.
Kawano, Hiroaki et al., "Histological study on the distribution of autonomic nerves in the human heart," Heart Vessels (2003) 18:32-39.
Lemery, Robert et al., "Feasibility study of endocardial mapping of ganglionated plexuses during catheter ablation of atrial fibrillation," Heart Rhythm. Apr. 2006; 3(4):387-96.
Liang, Zhao et al., "Selective Atrial Vagal Denervation Guided by Evoked Vagal Reflex to Treat Refractory Vasovagal Syncope," Pacing Clin Electrophysiol. 2012, e214-8.
Oh, Seil et al., "Complex Fractionated Electrograms and AF Nests in Vagally Mediated Atrial Fibrillation," Pacing Clin Electrophysiol. Dec. 2010; 33(12):1497-503.
Pachon M., Jose C. et al., ""Cardioneuroablation" e new treatment for neurocardiogenic syncope, functional AV block and sinus dysfunction using catheter RF-ablation," Europace (2005) 7, 1-13.
Pachon M., Jose C. et al., "Simplified Method for Vagal Effect Evaluation in Cardiac Ablation and Electrophysiological Procedures," JACC Clin Electrophysiol. Oct. 2015; 1(5):451-460.
Pachon M., Jose C. et al., "A new treatment for atrial fibrillation based on spectral analysis to guide the catheter RF-ablation," Europace (2004) 6, 590-601.
Pachon M., Jose C. et al., "Syncopal High-Degree AV Block Treated with Catheter RF Ablation without Pacemaker Implantation," Pacing Clin Electrophysiol. Mar. 2006; 29(3):318-22.
Pachon M., Jose Carlos et al., "Catheter ablation of severe neurally meditated reflex (neurocardiogenic or vasovagal) syncope: cardioneuroablation long-term results," Europace (2011) 13, 1231-1242.
Pachón Mateos, José Carlos et al., "Radiofrequency Catheter Ablation of Atrial Fibrillation Guided by Spectral Mapping of Atrial Fibrillation Nests in Sinus Rhythm," Arq Bras Cardiol 2007; 89(3) : 124-134.
Pauza, Dainius H. et al., "Morphology, Distribution, and Variability of the Epicardiac Neural Ganglionated Subplexuses in the Human Heart," The Anatomical Record 259:353-382 (2000).
Rosso, Raphael et al., "Vagal Paroxysmal Atrial Fibrillation: Prevalence and Ablation Outcome in Patients Without Structural Heart Disease," Journal of Cardiovascular Electrophysiology vol. 21, No. 5, May 2010, pp. 489-493.
Scanavacca, Mauricio et al., "Selective Atrial Vagal Denervation Guided by Evoked Vagal Reflex to Treat Patients With Paroxysmal Atrial Fibrillation," Circulation. Aug. 29, 2006; 114(9):876-85.
Yao, Yan et al., "Endocardial Autonomic Denervation of the Left Atrium to Treat Vasovagal Syncope: An Early Experience in Humans," Circ Arrhythm Electrophysiol. Apr. 2012; 5(2):279-86.

* cited by examiner

EXTRACARDIAC AUTONOMIC NERVE STIMULATION

OBJECT OF THE INVENTION

The ExtraCardiac Nerve Stimulator and the ExtraCardiac Nerve Stimulation (ECANS) are, respectively, the apparatus and method to get remote nerve stimulation for medical applications. The system makes possible the stimulation without direct contact with the nerve based on special electrical wave. The remote nerve stimulation is extremely important for investigational and therapeutic proposals. The possibility of having this resource without surgical dissection, nerve exposure and tissue lesion with time-consuming process, is remarkable. This procedure relies on a settable stimulator with special features that releases a pulse wave with high frequency, very short pulse width, great amplitude, and precise current and time limitation connected to a special catheter, placed inside a vase or viscera. Frequency, pulse width, amplitude and time of application are operator adjustable to be effective against large patient variations, different anatomy, and areas of application. Special features prevent the application of the stimulus in the heart.

BACKGROUND OF THE INVENTION

Extracardiac autonomic nerve stimulation (ECANS) have been a possibility for diagnostic and control of therapeutic procedures. Stimulation of sympathetic ganglia may be of great value for cardiac arrhythmias study. Vagal stimulation has been rising clinical application for brain and cardiac disorders. Thus, there is a growing needed for the diagnostic autonomic nervous system stimulation. It is highly desirable to have a specific neurostimulator capable of getting autonomic nerve stimulation from the endovascular/intravisceral territory during diagnostic and/or therapeutic electrophysiological procedures. Parasympathetic denervation (PD) has been increasingly applied by ablation for treating vagal related atrial fibrillation (VRAF) and in cardioneuroablation (CNA) for treating cardioinhibitory vasovagal syncope, and functional bradyarrhythmias. Additionally, in the next years there will surely be a great interest in study the effect of VS over the brain for treating depression and epilepsy. However, the massive VS or stimulation of any part of the autonomic nervous system inside or near the heart may cause serious cardiac arrhythmias. This apparatus and method propose a safe way to study the immediate vagal or autonomic nerve endovascular/intravisceral stimulation effect, over the heart and the brain, making possible to have a diagnostic tool to see the results pre, per, and post therapeutic procedure.

Parasympathetic denervation has been applied in several ablation procedures, like in the VRAF ablation[1,2,3] or for treating functional bradyarrhythmias (CNA)[4]. The success of this approach depends on a correct definition of the target areas and on a sure evaluation of the denervation. In that way, several methods may be considered as the high-frequency endocardial stimulation[5,6] and atropine response abolition[7]. High-frequency endocardial stimulation aims the stimulation of neural fiber in the atrial wall[8] Even though it may be well applied during AF, it is more troublesome for sinus rhythm. The problem of this method is that it may be applied only in restricted areas and may cause undesired arrhythmias. Case there is a dislodgment of the catheter to the ventricle, it may cause immediate ventricular fibrillation that is a potentially lethal arrhythmia. On the other hand, atropine infusion results in lasting and significant autonomic changes that may hamper any complementary ablation in the same session. Furthermore, considering the increase of the sympathetic tone following the vagal ablation the response to atropine has low value as the heart rate was increased by the ablation. About the brain, there is still no specific study of the patterns resulting from huge vagus stimulation.

The method presented here proposes a way to reproduce a stimulation of the segments of the ANS, for example, a massive vagal effect, without neural dissection, by stimulating from inside of the internal jugular vein or from any other vein, artery or hollow viscera. As the most important corollary, it allows checking the efferent and afferent vagal responses. The former may be used for studying several cardiac arrhythmias and for checking the loss of vagal effect in the heart, following the parasympathetic denervation procedure. The latter may be used for studying the electrical brain patterns resulting from the massive vagal stimulation that may be used for forecasting the therapeutic vagal stimulation.

It is a extracardiac vagal stimulation (ECVS) carried out through endovenous cannulation of the internal jugular vein, by using any bipolar electrophysiological catheter, even the RF one, forwarded up to the jugular foramen in the internal Jugular vein[9].

SUMMARY OF THE INVENTION

The present invention provides a solution for the aforementioned problems, by a device according to claim 1, namely the ExtraCardiac Nerve Stimulator, and a method according to claim 3, namely the ExtraCardiac Nerve Stimulation (ECANS). In dependent claims, preferred embodiments of the invention are defined.

In a first inventive aspect, the invention provides a specific neural stimulator that makes possible neural stimulation without direct contact with the nerve, from a variable distance through several tissues. It may get neural stimulation from within vase or viscera and has very restricted features:

1. Stimulation Wave and Sensitivity Properties

The device provides a pulsatile electric current with the following features:

A. Fairly broad band of frequencies, from 10 to 100 Hz. The amplitude must be able to stimulate the ANS without direct contact as the stimulation electrode is located inside of vein, artery, or viscera. By this way, the amplitude ranges from 0 to 1.00V and must be adjusted according to the patient weight;

B. Extremely short pulse width (10 to 50 microseconds) to prevent any risk of tissue lesion.

C. Sensitivity circuit for visceral response detection

A typical application of this feature is the detection of vocal cord activity during vagal stimulation which is necessary to confirm vagus nerve stimulation when the heart is denervated. However, several other biological potentials can be similarly detected by this system depending on the physiology of the region in which ECANS is being applied. For this purpose, the circuit has sensitivity from 1 μV to 30 mV and a band filtering filter from 1 to 500 Hxz.

Apparatus

Remote Neurostimulator (ExtraCardiac Autonomic Nerve Stimulator)

This device is a specific neural stimulator that can get neural activation without direct contact with the nerve, from a variable distance through several tissues. It may get neural stimulation from within vasa or viscera and has very restricted features:

1. Frequency: As the ANS usually operates at relatively high frequency, it is necessary that the device can work with a fairly broad band of frequencies, from 10 to 100 Hz;
2. Pulse Width: The pulse duration must be extremely short (10 to 50 microseconds) to prevent any risk of tissue lesion;
3. Amplitude: This device must stimulate the ANS without direct contact as the stimulation lead is located inside of vein, artery, or viscera. For vagal stimulation, for example, it is placed inside of the internal jugular vein, Error! Reference source not found. Depend on anatomical variations and the patient body dimensions there could be very different energy demands. By this way, the released amplitude must be from 0 to 80V and must be adjusted according to the patient weight;
4. Tissue Safety: To avoid any risk of tissue damage, the system is supplied with a specific current limiting circuit in addition to the very short pulse width;
5. Safety for Heart.

Cardiac Electrical Potential Detection: The most critical complication of this system is to cause a serious cardiac arrhythmia. By this way, the device is provided of one cardiac electrical potential detection circuit that inhibit any stimulation case a suspected cardiac potential is detected;

Cardiac Capture Detection: Before releasing the high frequency stimulation the software proceeds a cardiac pacing with the same adjusted amplitude. Case there is capture of any cardiac chamber the ECANS is suspended;

Timer: The microprocessor that controls the device allows several fundamental time functions for system operation such as a preselection of a time interval in which there should be no detection of cardiac activity, and a timer that allows a pre-selection of the time during which neural stimulation will be applied.

In a second inventive aspect, the invention provides a Remote Neurostimulation is a method for allowing nerve stimulation from inside of a vein, artery, or a viscera without direct contact with the nerve with several possible applications:

A. Cardiac electrophysiological studies;
B. Neurophysiological studies;
C. Gastroenterological studies;
D. Electrophysiologic studies from any vase or viscera.

Method

The ECANS may be performed from very different vasa and/or viscera. However, in order to exemplify the method, we are presenting a first clinical application for control and checking the vagal denervation. The results of the efferent stimulation of the vagus may be easily recorded by using one electrocardiograph. However, very different recorders may be necessary depending on the viscera is being studied. The most obvious effect is on the heart in which momentary stopping may occur with vagal stimulation or increased heart rate with sympathetic stimulation. On the other hand, through the electroencephalogram, functional brain changes may be detected by afferent vagus stimulation. Finally, any viscera can be specifically monitored, directly or indirectly. As for example we can mention the kidneys whose stimulation of the autonomic innervation can cause increase of the blood pressure and changes of the urinary volume. These observations have great potential for the development of clinical diagnostic tests.

Applications for ECANS

The ECANS has important applicability in numerous situations for diagnosis and for therapeutic control of procedures that aim some degree of autonomic denervation.

1. Diagnostic extracardiac vagal stimulation that may be performed from the superior vena cava, internal jugular veins, pulmonary veins, pulmonary artery, aorta, bronchi, trachea, etc;
2. A division of the sympathetic nervous system can be stimulated from within the veins or renal arteries;
3. The stellate ganglion or ganglia of the sympathetic paravertebral chain may be stimulated from the endovascular of cervical, thoracic, or abdominal vasa;
4. The vagus or divisions of the sympathetic nervous system can also be stimulated from within the gastrointestinal system or pelvic viscera;
5. Similarly, the vagus or divisions of the sympathetic nervous system can also be stimulated from within abdominal vasa, like inferior vena cava, aorta, celiac vena or artery, mesenteric veins or arteries, etc.

Potential Complication

It is a crucial question as this kind of stimulation may have the potential of a severe complication by inducing atrial and/or ventricular fibrillation. Atrial fibrillation may be well tolerated, however ventricular fibrillation must be absolutely prevented. It is necessary to avoid any risk by the protection of a (CEPDU) Cardiac Electrical Potential Detection Unit that only releases the stimulation in the absence of any cardiac electrical activity.

All the features described in this specification (including the claims, description and drawings) and/or all the steps of the described method can be combined in any combination, with the exception of combinations of such mutually exclusive features and/or steps.

DESCRIPTION OF THE DRAWINGS

These and other characteristics and advantages of the invention will become clearly understood in view of the detailed description of the invention which becomes apparent from a preferred embodiment of the invention, given just as an example and not being limited thereto, with reference to the drawings.

DETAILED DESCRIPTION OF THE INVENTION

Figure 1:
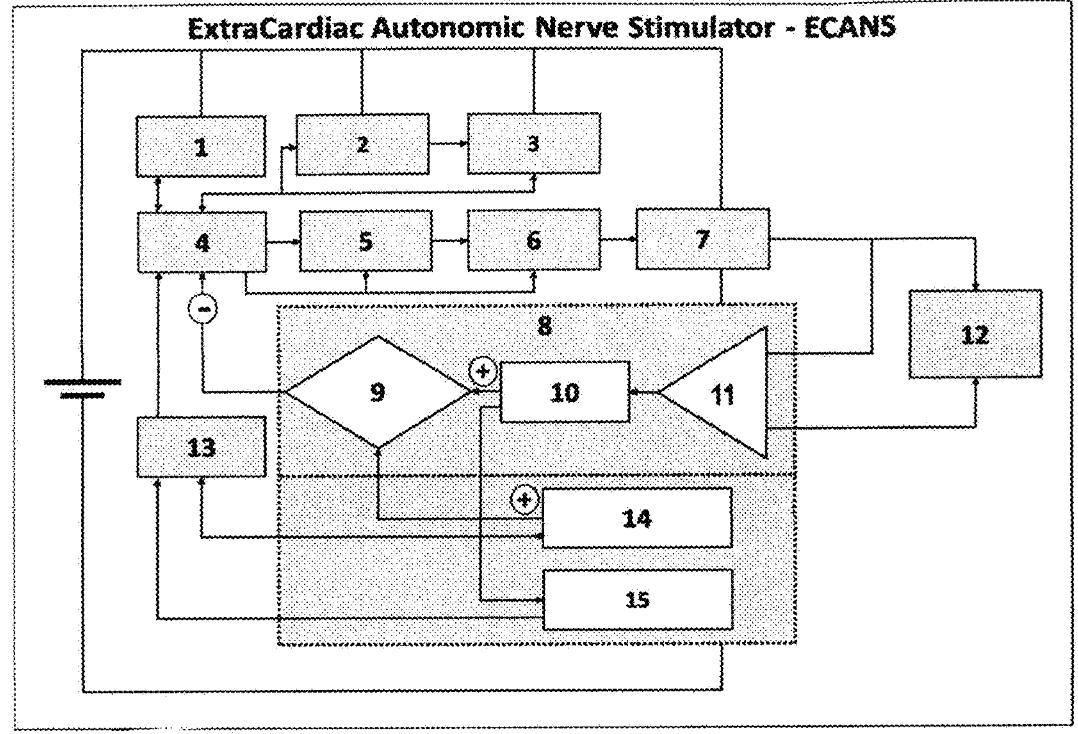
FIG. 1 This figure shows a simplified diagram of the ExtraCardiac Autonomic Nerve Stimulator—ECANS.

FIG. 1 shows a simplified diagram of the ExtraCardiac Autonomic Nerve Stimulator—ECANS.

This kind of stimulation may have the potential of a severe complication by inducing ventricular fibrillation. It is necessary to avoid any risk by the protection of a (CPDU) Cardiac Potential Detection Unit that only releases the stimulation in the absence of any cardiac electrical activity.

Figure 2:
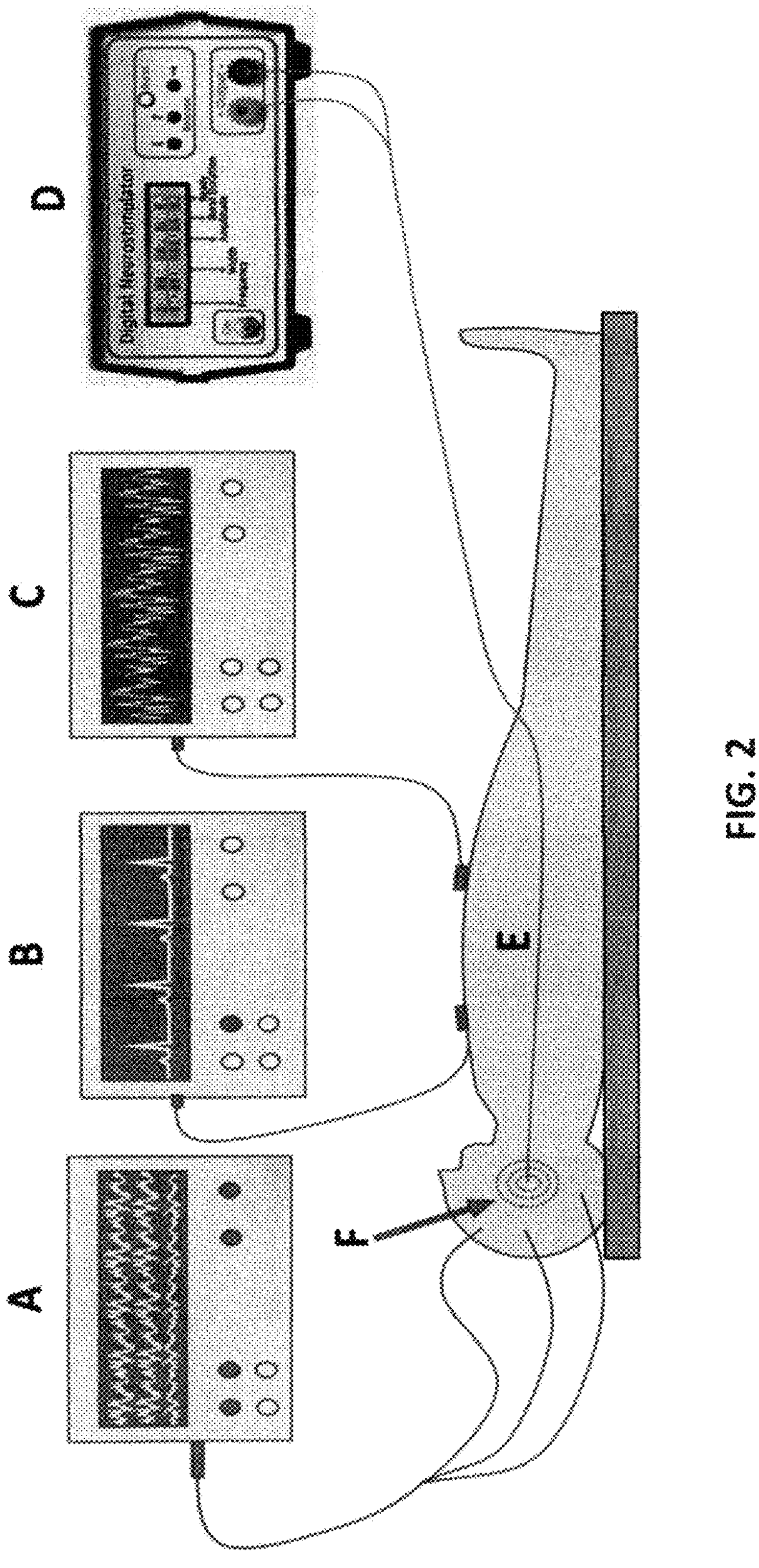
FIG. 2 This figure shows a scheme of the methodology for ECANS applications.

Particularly, it is represented:

1. Battery charger
2. Multifunction keyboard
3. Multifunction display
4. Microcontroller
5. Voltage step-up
6. Amplitude setup circuit
7. Current limiter
8. Electrical Potential Detection Unit
9. Logic detector
10. Filter
11. Amplifier
12. Extracardiac autonomic nerve
13. Master software
14. Cardiac capture detection software
15. Visceral capture detection software FIG. 2 shows a scheme of the methodology for ECANS applications.

Particularly, it is shown:

A: Electroencephalograph (EEG); B: Electrocardiograph (ECG); C: Visceral Monitor (VM); D: Neurostimulator for ECANS; E: electrode for ECANS that can be located inside a vein, inside an artery or inside a hollow viscera. In this example, the stimulation electrode is located inside the internal jugular vein at the level of the jugular foramen. The vagal stimulation at this point may cause several responses detected by the EEG, by the ECG and by the VM. This method can be applied from inside of other vasa because the nerves are usually very close to the vascular system. Any other ANS stimulation may cause effects that may be detected by A, B and C.

Figure 3:
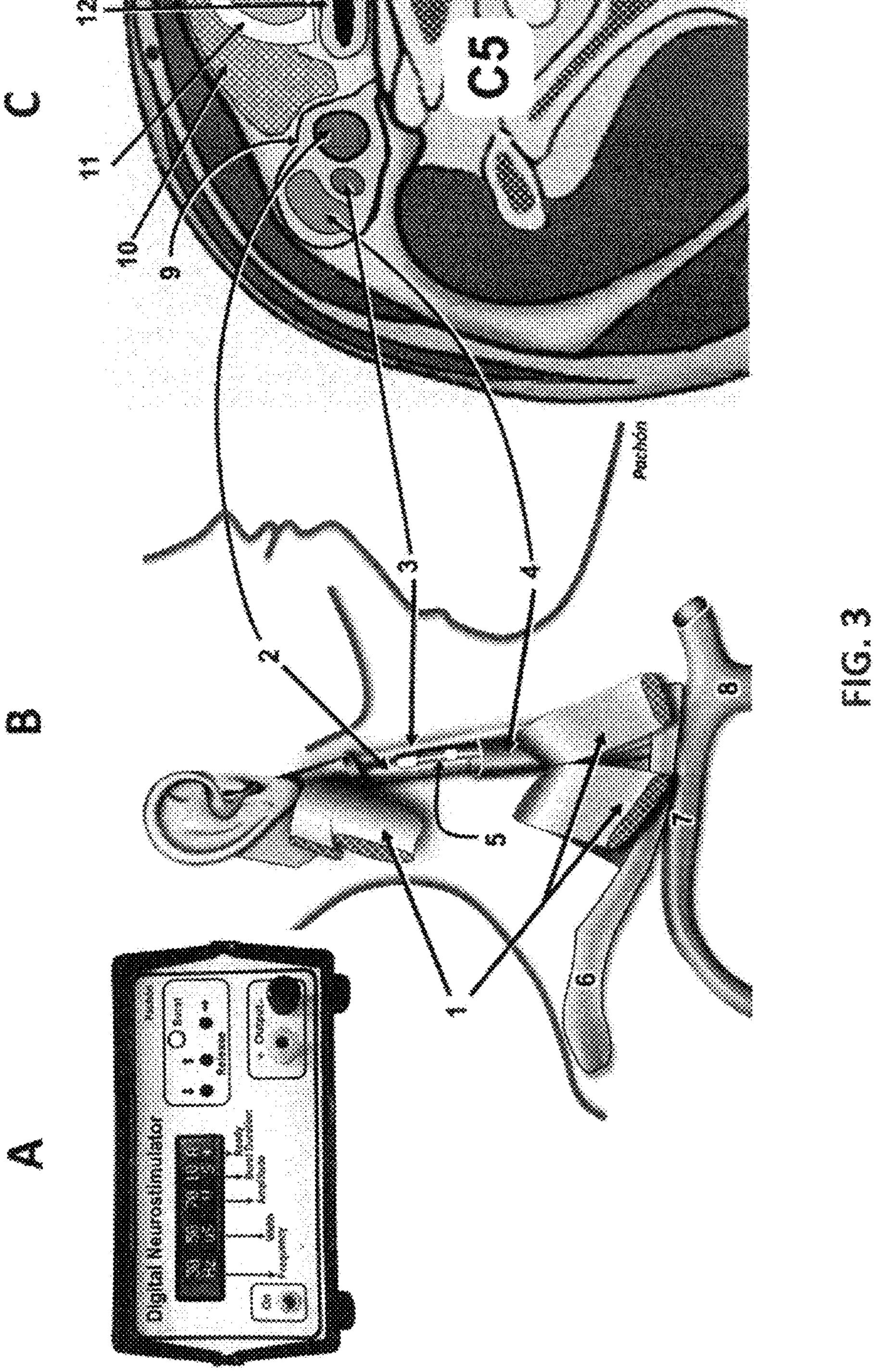
FIG. 3 This figure shows a neurostimulator for ECANS, an anatomical correlation of the vagus nerve and a transverse section of the neck showing the close relationship of the jugular vein, carotid artery and vagus nerve.

FIG. 3 shows a neurostimulator for ECANS, an anatomical correlation of the vagus nerve and a transverse section of the neck showing the close relationship of the jugular vein, carotid artery and vagus nerve.

Particularly:

1. Muscle sternocleidomastoid
2. Carotid artery
3. Vagus nerve
4. Right internal jugular vein
5. Neural stimulation catheter
6. Clavicle
7. Right subclavian vein
8. Superior vena cava
9. Carotid sheath
10. Thyroid
11. Trachea
12. Esophagus
13. Digital Neurostimulator C5. Fifth cervical vertebra A: Neurostimulator for ECANS. In this example it is being used for detecting preablation vagal innervation integrity and postablation denervation. The electrical features are commented in claims; B: Anatomical correlation of the vagus nerve. The catheter electrode is placed inside of the internal jugular vein with no direct contact with the nerve. The internal jugular vein was sectioned for didactic reason to facilitate the understanding of the method; C: Transverse section of the neck showing the close relationship of the jugular vein, carotid artery and vagus nerve. As the nerves lie near the vasa this method can be used for analogous stimulation in several other applications.

Figure 4:
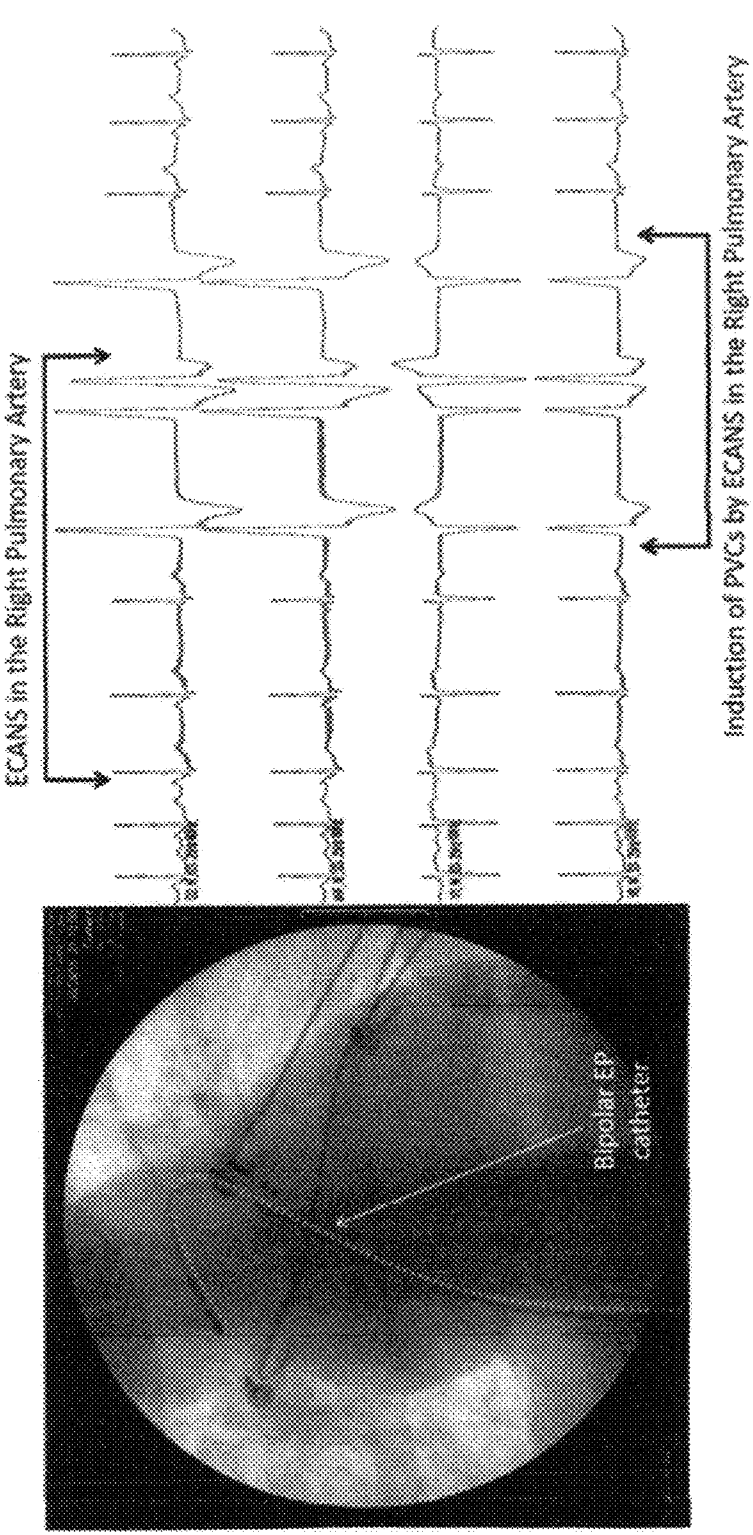
FIG. 4 This figure shows an example of ECANS.

FIG. 4 shows an example of ECANS, particularly a chest X-Ray during treatment of ventricular arrhythmia. This patient underwent ablation of very symptomatic premature ventricular ectopic beats (PVCs). After sedation, the PVCs disappeared. Despite having exhausted the classic maneuvers of arrhythmias re-induction, such as cardiac stimulation, isoproterenol infusion, reversion of sedation waking the patient, the PVC re-induction was only possible through stimulation of the autonomic nervous system from inside of right pulmonary artery by means of ECANS. This re-induction was reproducible, allowing successful mapping and ablation, confirmed by the absence of the arrhythmia in a long-term follow-up. At the end of ablation, a new ECANS showed the arrhythmia absence getting the immediate successful endpoint.

Figure 5:
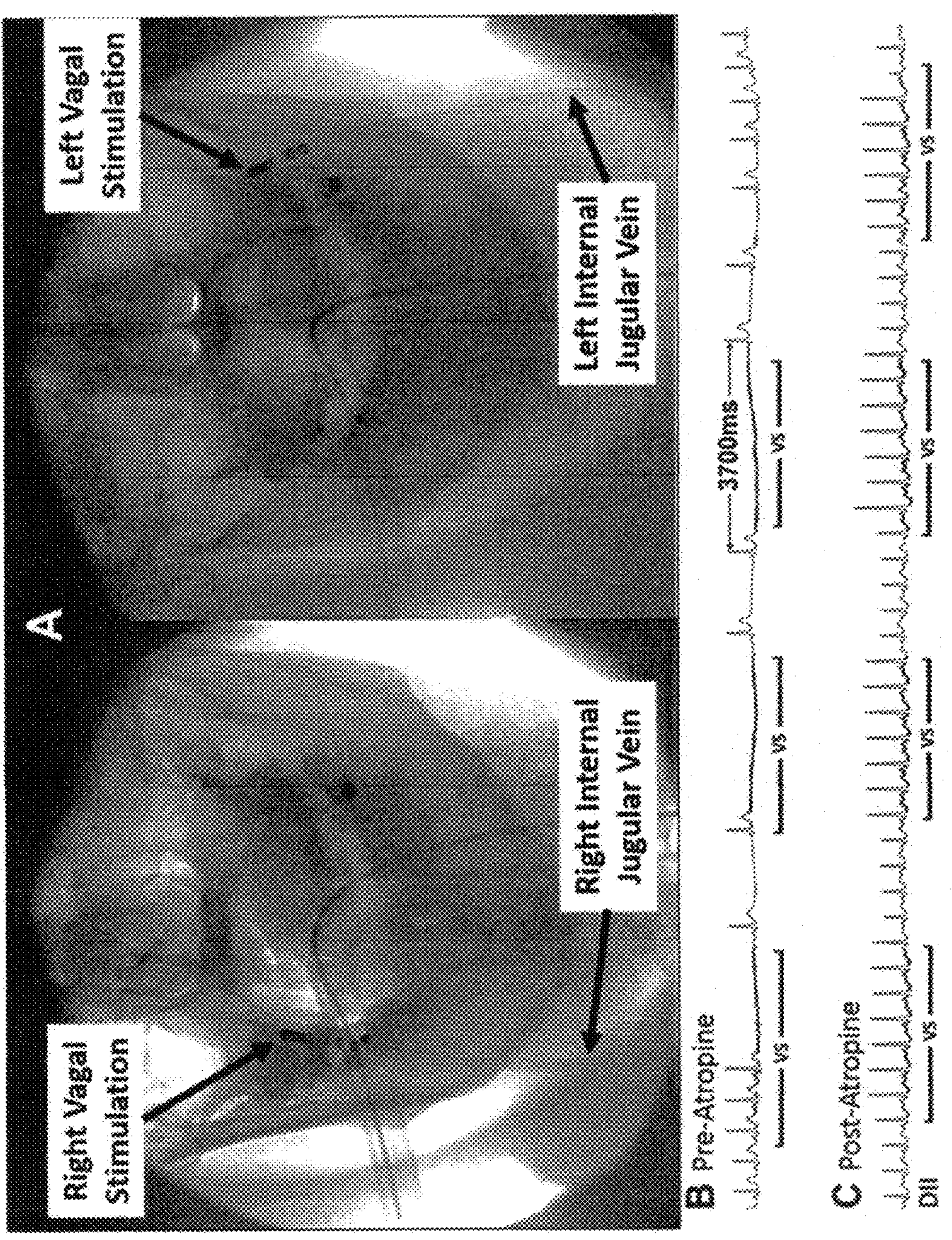
FIG. 5 This figures shows a fluoroscopy of the position of the RF catheter progressed into the right and left internal jugular veins to get appropriate proximity to the jugular foramen for VS.

FIG. 5 shows a fluoroscopy of the position of the RF catheter progressed into the right and left internal jugular veins to get appropriate proximity to the jugular foramen for VS.

Any new VS during the procedure was performed repeating identical radiological position. B and C: Example of repetitive vagal stimulation (VS) near the right jugular foramen pre and post-atropine. The right VS cause immediate sinus node arrest. After atropine, the vagal response is completely abolished.

Figure 6:
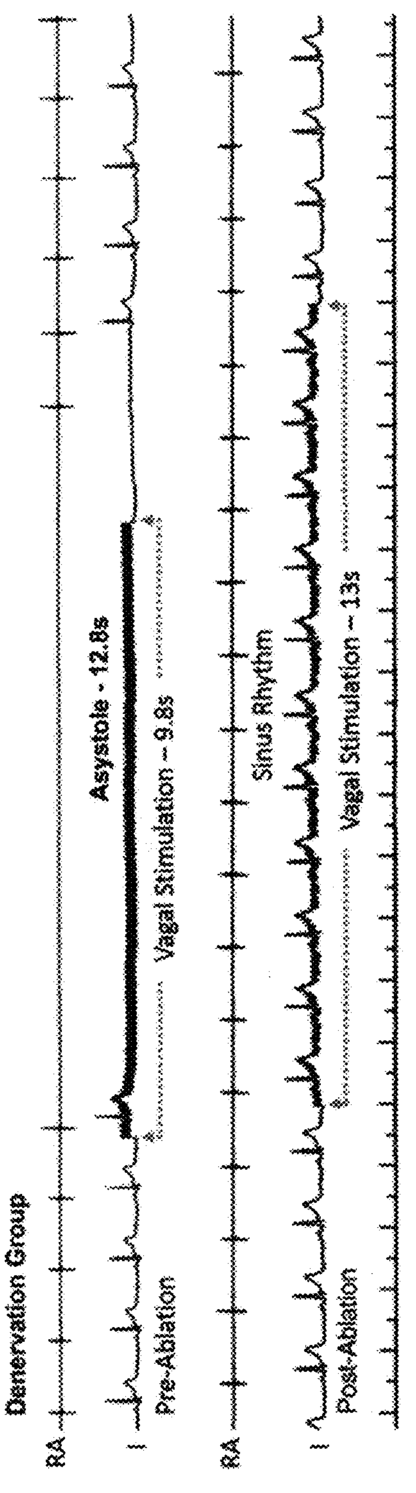
FIG. 6 This figure shows a graph with an example of a patient from Denervation Group presenting severe cardioinhibitory syncope. The upper strip shows 9.8 seconds of VS causing a pause (asystole) of 12.8 seconds, pre-ablation.

FIG. 6 shows a graph with an example of a patient from Denervation Group presenting severe cardioinhibitory syncope. The upper strip shows 9.8 seconds of VS causing a pause (asystole) of 12.8 seconds, pre-ablation.

The upper strip shows 9.8 seconds of VS causing a pause (asystole) of 12.8 seconds, pre-ablation. Following the vagal denervation the VS is repeated in the same place causing no pause (lower strip) demonstrating a clear vagal denervation. During the stimulation, the rhythm remains normal without any change in the heart rate and in the AV conduction. The complete absence of vagal response in these cases is considered the primary endpoint for this procedure.

Figure 7:
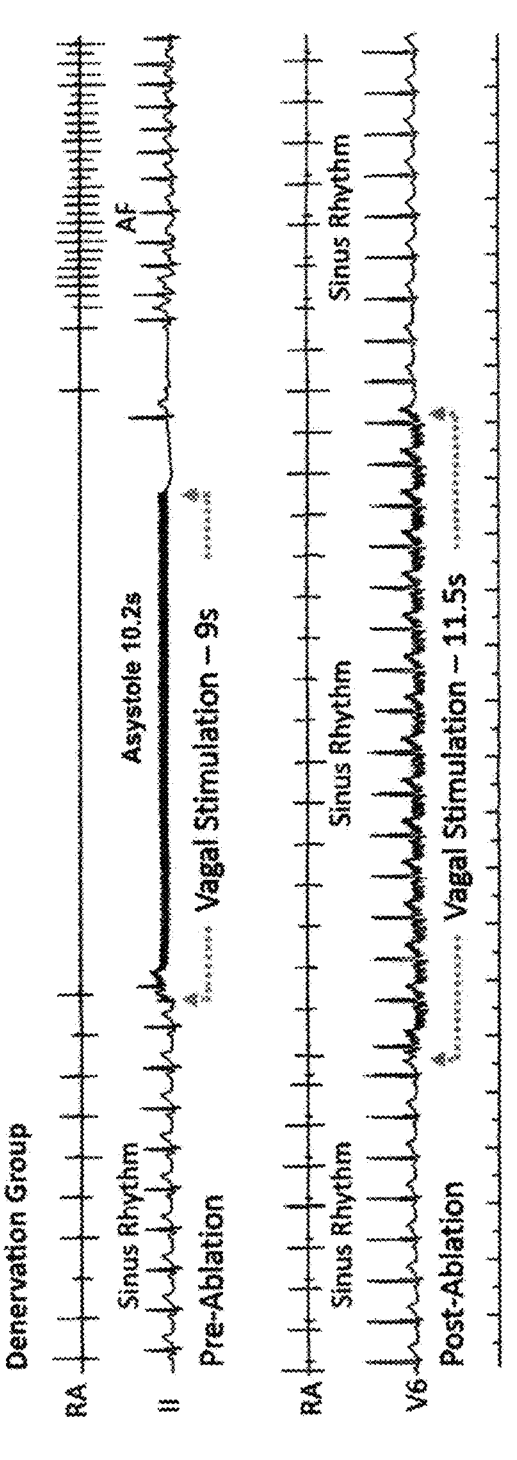
FIG. 7 This figure shows a graph with an example of a patient of the Denervation Group presenting AF typically related to the increase of the vagal tone.

FIG. 7 shows a graph with an example of a patient of the Denervation Group presenting AF typically related to the increase of the vagal tone.

The upper strip shows a VS during 9 seconds that causes immediate pause leading to an asystole of 10.2 seconds that was followed by a spontaneous induction of AF (AF). The right atrial channel (RA) shows the sinus rhythm on the left, the sinus pause in the middle and the AF on the right. This patient was treated with conventional AF ablation plus vagal denervation in order to abolish the vagal induction of the arrhythmia. At the end of the procedures, the VS was repeated for 11.5 seconds, and no pause and no AF were observed. There was a complete absence of the vagal response reaching an important immediate endpoint of the treatment.

Figure 8:
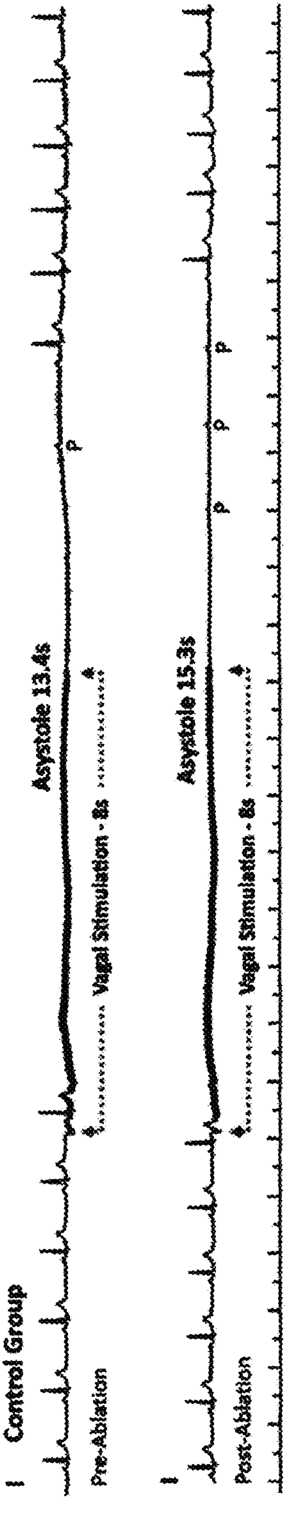
FIG. 8 This figure shows a graph with an example of the Control Group.

FIG. 8 shows a graph with an example of the Control Group.

This patient had a very symptomatic ventricular ectopic beats that was successfully treated by RF ablation in the right ventricle. Before ablation, 8 s of VS caused a pause of 13.4 s. Following the ablation, a new VS of 8 s produced another pause of 15.3 s. This assay shows the reproducibility of this VS method and also shows that there is no change in the vagal function in cases without autonomic ablation.

Figure 9:
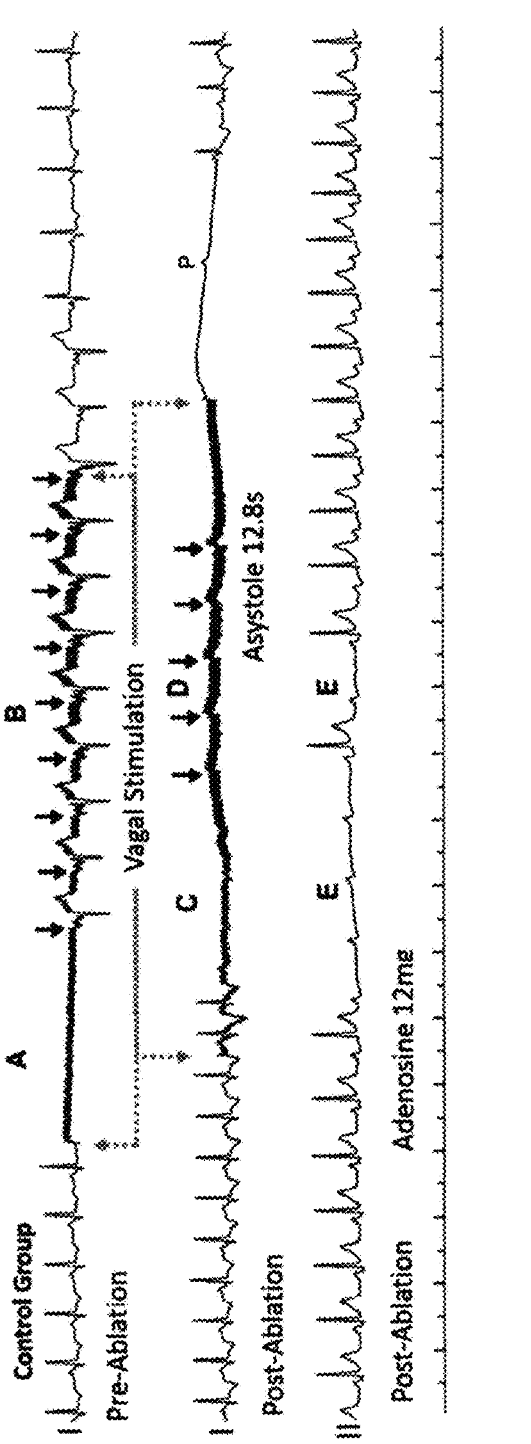
FIG. 9 This figure shows a graph of a patient from Control Group with ablation not aiming vagal denervation. He was included to test the VS pre and post-WPW ablation.

FIG. 9 shows a graph of a patient from Control Group with ablation not aiming vagal denervation. He was included to test the VS pre and post-WPW ablation.

He was included to test the VS pre and post-WPW ablation. In this case, the ablation had no intention of autonomic denervation. In the upper strip, VS was applied during 10 seconds. Just at the beginning there is immediate sinus pause (A), followed by a short period of atrial pacing (dark arrows) during VS (B). At this moment, despite the nodal block, the patient presents conduction over the accessory pathway, as it is not depressed by the vagal action. The previous short QRS (unapparent WPW) became aberrant revealing the presence of the anomalous conduction. The middle strip shows a new VS, at the end of the ablation, subsequently the accessory pathway elimination. There is a long asystole (12.8 s) beginning in C, showing that the conventional ablation without denervation preserves the vagal function. In D, was performed a short period of atrial pacing (dark arrows) showing functional transitory complete AV block, caused by the vagal action and absence of the abnormal conduction. In the lower strip it is shown short AV block (E) induced by adenosine, proving the lack of abnormal conduction. This effect is similar to the atrial pacing during VS. The latter can be useful in cases with adenosine contraindication. P: blocked P wave due to the vagal effect.

Study Showing One Clinical Application of Ecans

The aim of this study is to show the method that comprises the ECANS by using, as an example a simplified approach to check the vagal innervation and, also, confirming the vagal denervation, any time, during ablation or diagnostic procedures. The endpoint depends on the complete vagal denervation that ends the procedure.

Study Design

It is a prospective controlled study constituted of two groups: the "Denervation Group" (DG) underwent ablations targeting vagal tone reduction and another group submitted to conventional ablations known do not interfere with vagal tone "Control Group" (CG). Both were submitted to a similar routine of catheter RF ablation. VS were identically performed before and after ablations to compare the results in both groups. The control group was included to verify whether the autonomic changes obtained at the end of the intervention resulted from a real denervation or if were a nonspecific ablation outcome.

Patients and Method

Recruitment of patients began on Jul. 6, 2013 and ended on Dec. 17, 2014. 64 patients without significant structural heart disease (48 male/75.0%, 46.4±16.4 years-old), having symptomatic arrhythmias and a well-defined indication for radiofrequency ablation, were included. Written informed consent was obtained from all patients prior to the procedure. They were distributed in the DG, with indication for ablation with autonomic intervention (vagal denervation for treating AF clinically related to vagal tone or severe cardioinhibitory syncope) and in the CG, with ablation indication without autonomic intervention (accessory pathways or benign ventricular ectopic beats and/or idiopathic ventricular tachycardia). General features of the patients are depicted in the following Table 1:

TABLE 1

| Baseline demographic and clinical data of patients. | | | |
|---|---|---|---|
| Total | Patients | 64 | |
| | Male/Female | 48/16 | 75%/25% |
| | Age | 42.5 ± 8.7 | y/o |
| Denervation Group (Ablation with Vagal Ablation) | N | 47 | |
| | Male/Female | 37/10 | 78.7%/21.3% |
| | Age | 50.3 ± 15.2 | y/o |
| | Ablation Indication | | |
| | VRAF | 40 | 85.1% |
| | Severe cardioinhibitory syncope | 7 | 14.9% |
| Control Group (Ablation without Vagal Ablation) | N | 17 | |
| | Male/Female | 11/6 | 64.7%/35.3% |
| | Age | 35.6 ± 15 | y/o |
| | Ablation Indication | | |
| | Benign VEB/Idiopathic VT | 4 | 23.5% |
| | Accessory pathways | 13 | 76.5% |
| Follow-up for VS | | FU = 8.8 ± 5 months | |

VRAF: Vagally Related Atrial Fibrillation;
VEB: ventricular ectopic beat,
VT: ventricular tachycardia In DG, there were included 47 patients having severe cardioinhibitory syncope or AF clinically associated with high vagal tone submitted to vagal denervation (vagal denervation aimed and performed) as previously published methodology[4,10]. The control group included 17 patients that underwent conventional ablation of accessory pathways, symptomatic benign premature beats or idiopathic non-sustained ventricular tachycardia (vagal denervation not aimed and not performed).

Inclusion Criteria for the Denervation Group:

1. Absence of significant structural cardiopathy;
2. Severe cardioinhibitory syncope or VRAF (AF clinically related to increased vagal tone: during sleep, at rest after meals and in the physical exercise recovery);
3. Severe cardioinhibition confirmed by head-up tilt-test or Holter with symptoms reproduction or AF recording related to high vagal tone;
4. Pacemaker indication at least by one clinician as a consequence of clinical treatment refractoriness in case of neurocardiogenic syncope;
5. Refractoriness at least to two antiarrhythmic drugs in case of AF;
6. Positive response to atropine test (0.04 mg/Kg IV atropine up to a maximal dose of 2 mg, doubling the heart rate or heart rate reaching more than 100 bpm at least for 15 minutes);
7. Absence of a metabolic or systemic disease that could be the syncope or AF origin.

Inclusion Criteria for the Control Group:

1. Absence of significant structural cardiopathy;
2. Frequent symptomatic ventricular ectopic beats and/or non-sustained monomorphic ventricular tachycardia with indication for catheter RF ablation or symptoms or risk related to an accessory pathway with guideline ablation indication;
3. Absence of a coronary, inflammatory, metabolic or systemic disease that could be the arrhythmia origin.

Materials

Irrigated RF ablation catheter (J&J), Daig duodecapolar catheter, St Jude transseptal puncture system, Daig circular decapolar catheter, customized neurostimulator and other support systems as: Navx electroanatomic system, Medtronic Atakr® II RF Generator system, BIS spectral system, Anesthesia Drager workstation, intraesophageal echocardiography, intraesophageal multipolar thermometer and GE OEM radiological workstation.

Vagal Stimulation

For the first trial, the stimulation was obtained by the endovascular electrical field created in the internal jugular vein from the distal and the third pole of the ablation catheter, temporarily used as a stimulation catheter detached from the RF generator, FIG. 3-B.

There was no contact with the vagus nerve. As the closeness between the nerve and the catheter in the internal jugular vein may have some variance, it was used an energy of 0.5 to 1 V/Kg limited to 70 Volts, with 30 Hz and a remarkably short pulse width of 50 μs.

Methods

Technical details of the several ablation procedures, like AF ablation, vagal denervation, accessory pathway ablation or ventricular ectopic beats or ventricular tachycardia ablation will not be addressed in this study as they are comprehensively considered in the bibliographic references and are not the aim of the present article. All cases were treated with intravenous anaesthesia with propofol under endotracheal intubation and BIS index control.

Bilateral VSs were identically performed before and after ablation in both groups having the results recorded for comparison. All the stimulations were carried out with BIS index from 40 to 50 in order to avoid significant autonomic depression, to have similar autonomic tone in all evaluations and to ensure comfort and safety for patients.

Vagal Stimulation

Despite having no specific catheter, for the first trial, in the supine position, the irrigated ablation catheter detached from the RF generator, was progressed into the internal right jugular vein up to the level of the upper wisdom tooth, FIG. 2 and FIG. 5. The neurostimulator was temporarily connected between the distal and the third pole of the RF catheter. From this point, with the catheter slightly turned to medial direction, short stimulations and minor adjustments were performed to search the position for maximum response based on the sudden cardioinhibition (sinus arrest or bradycardia and/or AV block) induction, FIG. 5-B. Afterward, it was performed the same type of VS in the left internal jugular vein. The best response points were marked with fluoroscopy where 8 to 12 seconds stimulation was performed and recorded on each side. Identical VSs were made post-ablation.

According to FIG. 5, it is shown:

A—Denervation Group—These patients underwent a vagal denervation [4] or vagal denervation with complete AF ablation[10], according to the methodology previously described and published aiming the vagal response elimination or reduction. The AF ablation was performed with three sequential steps: 1. Conventional Pulmonary vein isolation; 2. AF-Nests ablation and 3. Residual tachycardia ablation when induced at the end of the procedure. The AF-Nests were defined as areas of the atrial wall having fibrillar myocardium with segmented spectrum in the frequency domain or fractionated potentials in time domain by filtering the signal from 300 to 500 Hz [4,10,10,11,16,17,18,19,20]. A duodecapolar catheter was placed in the coronary sinus, and the left atrium was accessed by transseptal puncture. The 3D left; and right atrial anatomy was acquired by Navx system in a very similar procedure of a conventional AF ablation. Intravenous heparin was used to keep the activated coagulation time from 300 to 400 s.

The ablations were essentially applied to the PV insertion, AF-Nests and over the areas overlapping the GPs:

1. Area of the SRPV-GP through the left atrium (from the insertion of the right superior pulmonary vein to the interatrial septum up to the puncture area);
2. Antrum of the pulmonary veins with complete PVI in the AF group;
3. Coronary sinus roof through the left atrium aiming additional denervation of the IVC-GP;
4. Area of the SVC-GP (medial lower part of the superior vena cava) reached by the right atrium and;
5. Area of the IVC-GP by the right atrium (medial upper portion of the inferior vena cava up to the coronary sinus ostium);
6. AF-Nests located in the left and right surface of the interatrial septum and in the christae terminalis.

At last, new VSs were accomplished at the same place of the pre-ablation ones. Case there were observed any degree of vagal response, the ablation was revised and resumed searching for AF-Nests that inadvertently were not treated in the first stage. Again, VSs were performed up to complete elimination of the vagal response.

To finish, having confirmed the absence of vagal response, these patients underwent an additional atropine test (infusion of 0.04 mg/kg up to 2 mg) observing the cardiac rate by 15 minutes.

B—Control Group—These patients underwent a conventional ventricular ablation for treating an accessory pathway or for treating very frequent ventricular ectopic beats and/or idiopathic ventricular tachycardia. Transseptal approach was not necessary, and the ablations were restricted to the ventricular wall. Three catheters were used, one for coronary sinus mapping, one for ventricular pacing and other for ablation (J&J irrigated RF catheter). Similarly to the DG, before and after ablations, there were performed VS for 10 s with recordings and evaluations of the responses.

Statistical Analysis

Quantitative data are shown as the mean value±standard deviation. Normality was evaluated by the Kolmogorov-Smirnov test. Paired or non-paired samples two-tailed t-test were applied to establish comparisons between continuous data before and after ablation. Statistical analysis was performed using IBM SPSS Statistics Version 19 software. All values were considered statistically significant at two-tailed p value less than 0.05.

Results Most cases had easy bilateral access to the internal jugular. VS was easily obtained at several points from the jugular foramen to the level of the posterior arch of the third rib, however stimulations at lower levels cause significant and undesirable stimulation of the brachial plexus, which can be prevented by using the upper approach near the foramen jugular. In all but two patients, the bilateral VS was obtained. It was possible to place the catheter and to stimulate very quickly each side, in two to five minutes.

All the patients but one developed asystole. Only one developed transitory total AV block. In this case, the response to right VS was poor, but the left VS produced a consistent transitory total AV block allowing evaluation the vagal denervation. In another case, there was an anatomical barrier to reach a good left VS. All patients were closely monitored and there was no case of symptoms or signs related to neurostimulation or vascular injury in a median follow-up of 8.8±5 months. The ablation extension was determined by the complete elimination of the vagal response to VS. The results of the DG and CG are presented in Table 2.

In WPW patients, it was performed atrial pacing during VS-post-ablation in order to prove the accessory pathway elimination. The result was the same obtained with the adenosine test: the preexcitation was eliminated in all patients but one that was successfully treated in the same session with additional ablatidn. There were no complications.

DISCUSSION

A simple method of VS during electrophysiological procedures is very timely and appropriate right now, due to the worldwide increase in autonomic cardiac interventions [11, 12, 13, 14]. In the first cardioneuroablation study [4], it was employed the intravenous atropine to determine whether the vagal denervation was complete. Additional ablation had to be performed in case of response. However, the long autonomic atropine effect (average half-life of 4.1 hours) made it difficult any further evaluation. For this reason, a simplified VS that can be repeated any time during stepwise ablations causing no persistent autonomic interference seems to be attractive.

Because of the steerability for vein catheterization, the RF-catheter was elected for VS detaching it from the RF generator, though, any other electrophysiology catheter could also be used for this purpose depending on the convenience of the operator.

TABLE 2

Results pre and post-ablation. 10 patients in VRAF group and 2 in accessory pathway group presented spontaneous AF after asystole. In ventricular arrhythmia group 2 patients presented ventricular ectopic beats and 1 presented non-sustained ventricular tachycardia following the VS.

| | Group | P | Age | Diag | Vagal Resp Pre | Pause Pre | Proc | Vagal Resp Post | Pause Post | Drug Test |
|---|---|---|---|---|---|---|---|---|---|---|
| DG | VVS | 7<br>(5M) | 35.7 ± 13.0 | SCIS | Asy or<br>AVB | 12.4 ± 2.2 | CNA | None | 0 | Atropine<br>No resp |
| | VRAF | 40<br>(32M) | 52.9 ± 14.2 | VAF | Asy or<br>AVB/<br>AF(10) | 11.3 ± 1.8 | AF Abl +<br>CNA | None/No<br>AF | 0 | Ø |
| CG | AP | 13<br>(10M) | 32.0 ± 14.0 | 7WPW<br>6CAP | Asy or<br>AVB/<br>AF(2) | 11.5 ± 2.3 | AP<br>Abl | Asy<br>or<br>AVB | 11.3 ± 2.1 | Adenosine<br>TCAB |
| | VA | 4<br>(1M) | 47.5 ± 13.4 | VEB/<br>NSVT/IVT | Asy or<br>AVB/<br>VEB/NSVT<br>(3) | 11.3 ± 2.0 | Abl<br>VEB/VT | Asy<br>or<br>AVB | 11.3 ± 2.1 | Ø |

DG: Denervation Group;
CG: Control Group;
VVS: vasovagal syncope;
AF: atrial Fibrillation;
AP: accessory pathway;
VA: ventricular arrhythmia;
Diag: Diagnostic;
SCIS: severe cardioinhibitory syncope;
VAF: VRAF;
WPW: apparent accessory pathway;
CAP: Conceoled Accessory Pathway;
VEB: Ventricular Ectopic Beat;
NSVT: Non-Sustained Ventricular Tachycardia;
IVT: Idiopathic Ventricular Tachycardia;
Resp: Response;
Asy: Asystole;
AVB: AV Block;
CNA: Cardioneuroablation;
Abl: Ablation;
Ø: not necessary;
TCAB: Transitory Complete AV Block.
Comparison of preablation pauses of DG vs. CG: $p = 0.79$;
Comparison of pauses pre and post-ablation in CG: $p = 0.84$.

According to FIGS. 6-8:

Both groups presented a massive vagal response before ablation that completely disappeared in the DG following ablation. However, in the CG this vagal response persisted practically without modification (pauses comparison pre and post-ablation: p=0,79). The pre-ablation response was not significantly different between groups (p=0.84). 14 patients of the DG (29.8%) presented some degree of vagal response post-ablation that was completely corrected by resuming the ablation of the targeted areas in order to ablate additional AF-Nests in the same session. In all patients with cardioinhibitory syncope, atropine test was normal pre-ablation (inclusion criterion) and became negative post-ablation in all cases (the heart rate changed no more than one beat/minute).

As the sympathetic fibers regenerate in few months, the term "Parasympathetic Denervation" could be correct only for the late phase. In acute phase, there are both, a parasympathetic and a sympathetic denervation (autonomic denervation) however by using the VS of this study we could test only the vagal (parasympathetic) denervation. The sympathetic one was not accessed.

The feasibility and the immediate effect of this stimulation could be quickly observed before and after the electrophysiological procedures. Nevertheless, it is essential to assess whether the electrophysiological manipulation would cause some residual undesirable influence on the VS response. Therefore, we rationalize the study, including a "Denervation Group" based on CNA, whose primary objective is the vagal denervation, and a "Control Group" in which there would be performed extensive electrophysiological manipulation, but without aiming vagal denervation. The results showed that VS was easily obtained, was repeated during and at the end of the procedures and was quite useful for evaluating electrophysiological parameters. The stimulation was reliable as it was not changed by anesthesia and EP handling showing specificity for vagal denervation. In addition, VS was found to be a harmless, having no residual effect in a mean FU of 8.8±5 months and it was also an inexpensive alternative with high potential for employment in the diagnostic, therapeutic and investigational electrophysiology.

VS also comes for completing an important complement for the possibility of attaining a significant, persistent or permanent vagal denervation through catheter RF ablation. That may be of interest as it can potentially allow the treatment of functional bradyarrhythmias without pacemaker implantation [11]. The long-term outcomes of this therapy are showing remarkable results, reinforcing its potential therapeutic value [12]. Nevertheless, its success depends on the correct demarcation of the sites that allow the extensive and long-lasting parasympathetic denervation. In this sense, it is essential to eliminate the cell body of the postganglionic parasympathetic neuron, widely spread in the atrial walls (AF-Nests) and cardiac GP [15, 16]. Indeed, the atrial conventional ablation, mainly the AF ablation, eliminates cell bodies of parasympathetic postganglionic efferent neurons and the neuronal fibers of the sympathetic efferent and sensory afferent. Several studies have been showing that the fibers regenerate case the cell body is preserved. Thus, although there are sympathetic and sensory reinnervation, an extensive and permanent parasympathetic denervation can be observed due to elimination of the parasympathetic postganglionic cell bodies neurons located in the atrial walls (AF-Nests) and even in the GP. That is the main purpose of this technique. However, the success depends on absolute confirmation of wide vagal denervation that can be progressively tested during the ablation by the method proposed here.

Another potential convenience of direct vagal denervation is in the treatment of the VRAF [1,2,4]. In these cases, validation of the vagal denervation after ablation seems to be a significant hint. Additionally, in this group it is very interesting the spontaneous appearance of AF following the asystole caused by the VS linking the AF trigger to the vagal tone change, FIG. 7. Additionally, we have observed that AF appearance can be highly increased by VS during isoproterenol infusion. However, it is not the aim of the current study.

Besides the spontaneous induction of AF, another potential usage of the VS was to detect the presence of a second accessory pathway during WPW ablation (mainly useful in cases with contraindication to adenosine), FIG. 9. Both, right and left VS cause immediate sinus depression, however for accessory pathway searching, the left VS is likely more appropriate as it usually causes functional AV block due to AV nodal inhibition. In this sense, the endovascular stimulation of the left pulmonary artery is another source for AV block induction with less effect over the sinus node.

In addition, VS may be helpful for supraventricular tachycardias reversion, VRAF reproduction and may even restart missed ventricular ectopic beats helping the pace-mapping and testing the ablation result.

All these potential benefits justify an easy, low cost, reliable and transient VS mainly if its effect vanishes in a few seconds, as the VS proposed in this study.

S Although being not the aim of the present article, as the vagal denervation is the "study model" in this research, it is timely to comment something about the mapping of vagal innervation. Beyond the PV antrum, the targets for ablation were defined by either, mapping the neuro-myocardial interface and anatomically overlapped regions of cardiac GP. The former was carried out based on the identification of AF-nests [17, 18, 19, 20] according to the methodology of the CAN [4,12]. As confirmed by other studies, the AF nests are present even in the absence of AF and represent areas of higher innervation density related to neuro-myocardial interface [21]. Thus, its elimination results in vagal denervation, previously shown in the initial study by the abolishment of the atropine response. Mapping was complemented with RF application in anatomic regions related to the main cardiac GP. Beyond the AF-Nest mapping, functional studies have confirmed that there are three main parasympathetic GP located in epicardial fat pads [22]. Most of the vagal innervation of the sinus node originates from the SVC-GP and SRPV-GP, whereas most vagal innervation of the AV node originates from the IVC-GPthird GP. Thus, it is possible to get a wide vagal denervation by ablating anatomically the atrial endocardium overlapping the GP areas [22].

Study Limitations

In this study, we used the most intense vagal response, independent from the side; however, more detailed studies of vagal response from each side will be highly desirable. Non-simultaneous bilateral VS was the rule in CNA however, it was not performed in all the cases of VRAF and in the one with anatomical barrier.

Another important issue would be the study of the laterality of the VS that was not foreseen in this initial article, however, by using the present stimulation parameters, the VS caused both: a massive depression of the sinus node (asystole) and of the AV node (complete AV block), independent of the stimulated side. This suggests that there is probably, a great blend of fibers and both vagus innervate most of the GPs at end. The absolute requirement of bilateral VS cannot be elucidated with this study. Since in denervation both, sinus and AV node denervation are equally desired, a solution could be to stimulate one side two times: first without and second with atrial pacing. If both, asystole and total AV block are demonstrated, the contralateral vagal stimulation would not be necessary. This protocol was not made in this study as the focus was the VS feasibility.

This study did not include the long-term FU of denervation, accessory pathways or ventricular arrhythmias ablation because the aim was to show the immediate vagal effect under VS, its complete disappearance after acute vagal denervation and its maintenance without change on ablations without denervation.

CONCLUSION

In this study ECANS was explained and demonstrated by vagal stimulation from within the internal jugular vein, in the region of the jugular foramen. The vagal stimulation method by ECANS in this study was feasible, easy, reversible in a few seconds; harmless, reliable, low expensive and showed no complications. It seems to be a potential tool for the immediate confirmation of vagal or autonomic denervation, for evaluating the progression of the parasympathetic denervation during ablation and for autonomic tests during electrophysiological studies. The vagal denervation methodology used in this controlled study showed complete elimination of the vagal response. Ablation without denervation did not affect the vagal response indicating that this parameter is consistent and does not change with general anesthesia and electrophysiological handling.

The invention claimed is:

1. An extracardiac autonomic nerve stimulator for stimulating at least one nerve in a patient, the extracardiac autonomic nerve stimulator comprising:

a non-implantable neurostimulator configured to be positioned external to the patient;

a catheter electrode operationally coupled to said neurostimulator, wherein said catheter electrode is configured to be positioned within a vein, artery, or viscera of the patient in measurable but non-contact proximity with respect to the at least one nerve, said neurostimulator configured to output a stimulation pulse wave to the catheter electrode; and a Cardiac Electrical Potential Detection Unit (CEPDU) operatively coupled to said neurostimulator and said catheter electrode, said CEPDU configured to:

(i) detect a cardiac potential at said catheter electrode and inhibit release of said stimulation pulse wave to said catheter electrode upon detection of said cardiac potential at said catheter electrode; and (ii) before releasing said stimulation pulse wave, perform cardiac pacing with an amplitude adjusted by an operator, wherein said CEPDU suspends the release of said stimulation pulse wave upon detection of a cardiac capture;

wherein:

said CEPDU only releases said stimulation pulse wave to said catheter electrode in the absence of detection of any cardiac electrical activity;

in response to receipt of the stimulation pulse wave from said neurostimulator, said catheter electrode is configured to stimulate neural activation of the at least one nerve through tissues of the patient while not being in contact with the at least one nerve; and said neurostimulator is configured to adjust said stimulation pulse wave to have a frequency that is adjustable within a frequency range from and including 10 Hz to and including 100 Hz, to have a pulse width that is adjustable within a pulse width range from and including 10 microseconds to and including 50 microseconds, and to have an amplitude that is adjustable up to and including 80 V.

2. The extracardiac autonomic nerve stimulator according to claim 1, wherein the at least one nerve comprises ganglia.

3. The extracardiac autonomic nerve stimulator according to claim 1, wherein the extracardiac autonomic nerve stimulator is configured for use in analysis of electrophysiological cardiac responses by outputting the stimulation pulse wave that causes at least one of the electrophysiological cardiac responses detectable by one or more of: electrocardiogram (ECG) or visceral monitor (VM) operatively coupled with the patient.

4. The extracardiac autonomic nerve stimulator according to claim 1, wherein said neurostimulator comprises a pulse generating circuit capable of generating the stimulation pulse wave with variable and controlled frequency, amplitude, pulse width, and stimulation time limitations, such that the extracardiac autonomic nerve stimulator is always within a safe window for stimulation of the at least one nerve.

5. The extracardiac autonomic nerve stimulator according to claim 1, wherein said catheter electrode is configured to be only temporarily used for stimulation while being located inside of the vein, artery, or viscera of the patient.

6. The extracardiac autonomic nerve stimulator according to claim 1, wherein the extracardiac autonomic nerve stimulator comprises an electric current limiter configured to prevent release of high electric current by said neurostimulator.

7. The extracardiac autonomic nerve stimulator according to claim 1, wherein said neurostimulator comprises a multifunction display and a multifunction keyboard configured to allow an operator to modify operator preference parameters including the frequency, amplitude, pulse width, and pulse duration of said stimulation pulse wave.

8. The extracardiac autonomic nerve stimulator according to claim 1, wherein said extracardiac autonomic nerve stimulator is at least temporarily connected to said catheter electrode, and wherein any bipolar electrophysiological catheter is usable as said catheter electrode.

9. The extracardiac autonomic nerve stimulator according to claim 1, wherein the extracardiac autonomic nerve stimulator is configured to stimulate not only the at least one nerve, but is also configured to facilitate intravisceral stimulation.

10. A method of stimulating at least one nerve in a patient using an extracardiac autonomic nerve stimulator, the extracardiac autonomic nerve stimulator comprising a non-implantable neurostimulator configured to be positioned external to the patient, and a catheter electrode operationally coupled to said neurostimulator, the method comprising:

positioning said catheter electrode within a vein, artery, or viscera of the patient in measurable but non-contact proximity with respect to the at least one nerve;

outputting, using said neurostimulator, a stimulation pulse wave to said catheter electrode;

in response to receipt of said pulse wave from said neurostimulator, stimulating, using said catheter electrode, neural activation of the at least one nerve through tissues of the patient while not being in contact with the at least one nerve;

detecting, using a Cardiac Electrical Potential Detection Unit (CEPDU) operatively coupled to said neurostimulator and said catheter electrode, a cardiac potential at said catheter electrode and inhibit release of said stimulation pulse wave to said catheter electrode upon detection of said cardiac potential at said catheter electrode; and before releasing said stimulation pulse wave, performing cardiac pacing with an amplitude adjusted by an operator, wherein said CEPDU suspends the release of said stimulation pulse wave upon detection of a cardiac capture;

wherein:

said CEPDU only releases said stimulation pulse wave to said catheter electrode in the absence of detection of any cardiac electrical activity; and said neurostimulator adjusts said pulse wave by adjusting a frequency of said pulse wave so that said frequency is adjustable within a frequency range from and including 10 Hz to and including 100 Hz, by adjusting a pulse width of said pulse wave so that said pulse width is adjustable within a pulse width range from and including 10 microseconds to and including 50 microseconds, and by adjusting an amplitude of said pulse wave so that said amplitude is adjustable up to and including 80 V.

11. The method of stimulating at least one nerve in a patient using an extracardiac autonomic nerve stimulator according to claim 10, further comprising the step of removing said catheter electrode from the patient after the neural activation of the at least one nerve.

* * * * *